Figure 1:
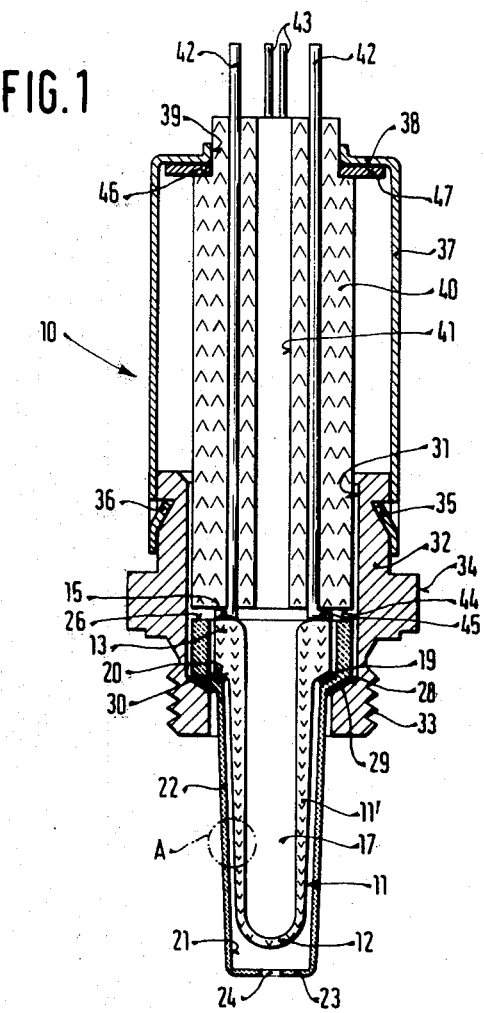

United States Patent [19]

Friese et al.

[11] 4,339,320

[45] Jul. 13, 1982

[54] HEATED GAS COMPOSITION SENSOR STRUCTURE

[75] Inventors: Karl-Hermann Friese; Friedrich Esper, both of Leonberg, Fed. Rep. of Germany

[73] Assignee: Robert Bosch GmbH, Stuttgart, Fed. Rep. of Germany

[21] Appl. No.: 193,944

[22] Filed: Oct. 6, 1980

[30] Foreign Application Priority Data

Oct. 20, 1979 [DE] Fed. Rep. of Germany ....... 2942494

[51] Int. Cl.³ ............................................ G01N 27/46
[52] U.S. Cl. ................................ 204/195 S; 23/232 E
[58] Field of Search .................... 204/195 S; 123/489, 123/549; 60/276; 23/232 E

[56] References Cited

U.S. PATENT DOCUMENTS

| | | | |
|---|---|---|---|
| 3,597,345 | 8/1971 | Hickam | 204/195 |
| 4,033,169 | 6/1977 | Fujishiro et al. | |
| 4,147,513 | 9/1977 | Bienkowski et al. | |
| 4,157,282 | 6/1979 | Riddel | |
| 4,178,222 | 12/1979 | Murphy et al. | 204/195 S |
| 4,212,273 | 7/1980 | Maruoka | 204/195 S |
| 4,251,342 | 2/1981 | Habdas et al. | 204/195 S |

FOREIGN PATENT DOCUMENTS

| | | |
|---|---|---|
| 52-156692 | 12/1977 | Japan . |
| 1217625 | 12/1970 | United Kingdom . |
| 1400579 | 7/1975 | United Kingdom . |
| 1420913 | 1/1976 | United Kingdom . |
| 1427361 | 3/1976 | United Kingdom . |
| 1472494 | 5/1977 | United Kingdom . |
| 1518943 | 7/1978 | United Kingdom . |
| 1534949 | 12/1978 | United Kingdom . |
| 2006440 | 5/1979 | United Kingdom . |

*Primary Examiner*—Howard S. Williams
*Attorney, Agent, or Firm*—Frishauf, Holtz, Goodman & Woodward

[57] ABSTRACT

To permit efficient heat transfer from a carrier tube (22) surrounding a tubular solid electrolyte body (11') having outer and inner electrodes (14, 18) applied thereto, the tubular heater element carrier body (22) supports a wire or resistance track heating element (25) at the inner surface thereof, the heater element (25) being spaced from the outer surface of the solid electrolyte tube (11') forming part of the sensor element (11) by a distance at the most of 1 mm, preferably less than 0.5 mm, the wall thickness of the heater element carrier tube (22) preferably being between 0.3 and 0.8 mm thick, the carrier tube being made of ceramic, such as aluminum oxide, or internally insulated metal.

11 Claims, 2 Drawing Figures

HEATED GAS COMPOSITION SENSOR STRUCTURE

The present invention relates to a sensor structure to determine the composition of exhaust gases and derive an electrical output signal representative thereof, which includes a heating element, and more particularly to a gas composition sensor to determine the composition of combustion gases, especially exhaust gases from internal combustion engines.

BACKGROUND AND PRIOR ART

Various types of electrochemical sensors are known utilizing an ion conductive solid electrolyte. Most of those sensors operate only at an elevated temperature, for example above 400° C., since the ion conductivity of the solid ion conductive elements is insufficient at a lower temperature. When used as an exhaust gas sensor in combination with internal combustion engines of the automotive type, even higher operating temperatures may be required to prevent impairment of operation of the sensor by lead contained in the exhaust gases. The output signal of the sensor is dependent on the temperature of the solid electrolyte. It has already been proposed to provide heating elements in combination with the sensors in order to reduce the response time of such sensors when exposed to cold gases and to obtain an output signal which can be readily analyzed and, further, to improve the lifetime of the sensor in the presence of exhaust gases from internal combustion engines which contain lead. Additionally, the accuracy of measurement is improved when the temperature of the element is high. It is thus desirable to supply heating elements to the sensors. The use of heating elements with such sensors is also indicated if the sensor is placed in positions in the exhaust system from internal combustion engines where the exhaust gases are already substantially cooled.

The sensor structure, which forms the basis of the structure of the present invention, is well known. Generally, the structure has been described, for example in U.S. Pat. No. 3,597,345. This type of sensor has a solid electrolyte tube which is closed at one end. A resistance heating element is provided, surrounding the closed tube with some distance. The resistance heater is a tubular element, positioned at the external or outer side of a tubular carrier body therefor. Such a sensor-heating element combination requires a specific and special type of heat insulation; the heating efficiency of the heating element is comparatively poor. The structure is expensive to make and thus is not suitable for mass production for automotive use and, further, difficulties arise with mounting of the various components in such a manner that they can withstand shocks and vibrations encountered in automotive applications.

THE INVENTION

It is an object to provide a heated gas composition sensor, particularly adapted for incorporation in the exhaust system of an automotive internal combustion engine, which can provide high heating with optimum efficiency, raise the temperature of the sensing element to appropriate levels and, overall, can form a structure which is essentially immune to deterioration even under the presence of severe shocks and vibrations, as encountered in automotive applications.

Briefly, the sensing structure itself utilizes a closed tube of solid ion conductive material, such as stabilized zirconium dioxide. In accordance with the invention, the heating element is applied to the inner wall of a tubular carrier in form of a carrier tube, closely surrounding the tubular solid ion conductive body. The spacing distance between the inner wall of the carrier tube on which the heating element is applied, and the outer surface of the sensing element tube itself at the most is 1 millimeter and, preferably, 0.5 mm or less. The carrier tube itself has a very thin wall between 0.3 and 0.8 mm thickness, and may be made of an insulating ceramic. The heater itself can be a meander or spiral resistance heater.

The structure has the advantage of excellent utilization of heat energy derived from the heating resistance wire or track formed on the carrier tube. Additionally, incorporation of the heating element in structures previously proposed is simple so that the heater element can be readily integrated with sensors designed for utilization in stock vehicles. The heater element—sensor combination, together, has a sturdy, vibration and shock-resistant construction which can be assembled comparatively inexpensively and is eminently suitable for mass production.

In accordance with a feature of the invention, and resulting in a particularly suitable structure, the carrier for the resistance heater element, simultaneously, can function as a protective tube to protect the solid ion conductive electrolyte body against damage or contamination from particles carried in exhaust gases of automotive engines.

The structure in accordance with the invention is not limited to sensors capable of determining the oxygen content in gases; it can be used, however, for all types of sensors sensing all types of gases, in which the output signals derived from the sensors are strongly temperature dependent.

The structure can be used not only with a closed solid electrolyte tube, in which the outer side is exposed to the gas, the composition of which is to be tested, and the inner side of the tube is exposed to a reference substance, for example the oxygen in ambient air. The present invention is also suitable for use with sensors in which, for example, both electrodes applied to the solid ion conductive body are exposed to the measuring gas—see, for example, U.S. Pat. No. 4,157,282, Riddel. The sensor can operate either as a voltage generating cell, that is, in potentiometric mode, or may operate as a polarographic sensor, in which the limiting current, upon application of a voltage to the sensor, is a measure of the gas composition, see, for example, U.S. Pat. No. 3,691,023, Ruka et al., and U.S. application Ser. No. 6,093, of Jan. 24, 1979, Dietz, to which German Published Patent Document DE-OS No. 27 11 880 corresponds. The structure may also be used with sensors using semiconductors, such as titanium dioxide (see German Patent Disclosure Document DE-OS No. 28 17 873; U.S. Pat. No. 4,147,513; U.S. Pat. No. 4,033,169). Adaptation of the structure in accordance with the present invention to those sensors is within the skill of the art. The sensor structure can also be used to determine the proportion of soot or carbon in gases, see, for example, U.S. Ser. No. 62,361, filed July 31, 1979, Sarholz).

Figure 2:
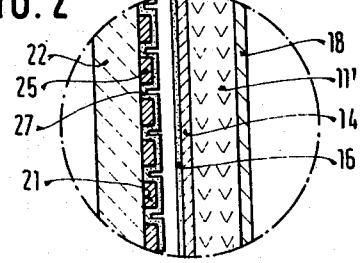

DRAWINGS:

FIG. 1 is a schematic longitudinal sectional view through an electrochemical sensor with an ion conductive solid electrolyte tube closed at the end, to an enlarged scale; and FIG. 2 is a greatly enlarged view of the area within the circle A of FIG. 1.

The sensor 10 has a sensing element 11 which is formed as an ion conductive solid electrolyte tube 11' made of stabilized zirconium dioxide. It has a closed bottom 12, forming an end portion adapted for exposure to the gas to be analyzed. At the connecting side of the tube—that is, at the other end thereof, the tube is formed with a flange 13. The outer surface of the solid electrolyte tube 11' has a porous catalyzing layer, preferably of platinum or a platinum metal, applied thereto which forms a measuring electrode 14 (FIG. 2) and which covers the region of the tube 11' at least in part, which is washed by the gases to be analyzed, and passes over towards the flange 13 and the edge surface 15 of the solid electrolyte tube 11. The measuring electrode 14 is protected from damage in the region where it is exposed to the gas by a porous protective layer 16, for example of magnesium spinel. Layer 16 protects the electrode 14 against damage due to mechanical and thermal attack by the sensing gases.

The surface facing the interior space 17 of the solid electrolyte tube 11 has a porous electron conductive track 18 applied thereto, forming a reference electrode. The reference electrode 18 likewise may be made of platinum or a platinum metal and extends from the bottom 12 of the closed solid electrolyte tube over to a portion 15 at the end face of the solid electrolyte tube which is electrically isolated from the region of the face 15 over which the measuring electrode 14 extends, so that the measuring electrode 14 and the reference electrode 18 are electrically isolated from each other.

The solid electrolyte tube 11' has the bottom side of its flange 13 applied to a ring-shaped seal 19. The sealing ring 19 may, for example, consist of heat resistant copper-coated steel. The sealing ring 19 connects the solid electrolyte tube 11' to an abutment surface 20, formed similar to a shoulder, on the inner surface 21 of a heater element carrier 22. The heater element carrier 22, preferably, is made of ceramic material, for example aluminum oxide. It is placed coaxially around the solid electrolyte tube 11'. The heater element carrier 22 is 0.6 mm thick, surrounds the solid electrolyte tube 11' in tubular manner, and, preferably, also has a bottom surface 23. The bottom surface 23 is formed with a passage 24 for the gas to be analyzed.

In accordance with the present invention, the inner surface 21 of the heater element carrier 22 has a heater element 25 applied thereto, in form of a spiral or meander shaped wire, or in form of a meander-shaped or spirally arranged conductive track or layer. The external terminals of this heater element, wire or layer, are carried to suitable connections—not shown in the figures—applied to the end face 26 of the heater element carrier 22. The heater element wire or layer, preferably, is additionally protected and covered by an electrically insulating protective layer 27 (FIG. 2), which increases the lifetime of the heater element and additionally prevents electrical short circuits due to the depositions of particles derived from the test gas.

The heater element 25 is secured to the carrier 22 by a suitable ceramic adhesive, if the heater element is in wire form; if the heater element 25 is applied to the inner surface 21 of the carrier 22 in form of a layer, then it is preferably applied by spray deposition, or printing or rolling-on of a suspension including conductive particles of the heater conductor material, using a mask or pattern. Another way of applying a layer to the inner side of the tube forming the carrier 22 is by applying a mask or pattern thereover and then dipping the heater element in a suspension containing heater conductor material particles.

In accordance with a feature of the invention, the heater element 25 and its carrier 22 are so dimensioned that the distance of the heater element 25 to the outer coated solid electrolyte tube 11' at the most is 1 mm; even smaller distances are preferred, for example 0.5 mm. In the example illustrated, the heater element 25 has a distance from the outer surface of the solid electrolyte tube 11' of 0.4 mm. The solid electrolyte tube 11' tapers slightly towards the closed bottom 12. It has an average diameter of about 6 mm. The arrangement of the heater element 25 on the carrier 22 results in particularly efficient heat transfer, and thus efficient use of heater power applied to the heater wire 25. The carrier 22 on which the wire is applied has a thickness of, preferably, between 0.3 and 0.8 mm.

Rather than using a ceramic carrier 22, as in the above example, a metallic carrier can be used which, then, must be supplied with an insulating coating or layer at its inner surface to permit application of the heater element 25 directly thereto, or the heater element 25 must be insulated.

In the example illustrated, the carrier 22 for the heater element simultaneously functions as a protective tube for the solid electrolyte body 11' and for its measuring or sensing electrode 14. Alternatively, it is also possible to add an additional protective tube over the carrier 22', formed with suitable openings to permit ingress of test gas. Such an additional coaxially positioned tube then permits use of a heater element carrier 22 which does not have a bottom 23 but, rather, is merely an open tubular element.

A shoulder 28 is formed on the outside of the heater element carrier 22, supporting a ring-shaped seal 29 which, again, preferably, is a heat resistant, copper-coated steel ring. The sealing ring 29 is seated on a shoulder 30 of the through-bore 31 of a metallic housing 32. Housing 32 is made of a heat resistant metal, for example heat-resistant steel, and is formed on the outside thereof with an attachment screw thread 33 and a wrench-engaging surface 34, for example similar to a spark plug, to permit assembly of the sensor 10 to project into a duct carrying exhaust gases from an internal combustion engine (not shown).

The housing 32 is formed with internal recesses 35 into which internally projecting lugs or lips 36 of a metallic sleeve 37 are engaged. Sleeve 37 forms a protective extension leading towards the end portion of the sensor. It is formed with a closed end portion 38 having a central opening 39 therethrough.

A ceramic spacer and support body 40, for example made of aluminum oxide and formed with a longitudinal opening 41 therethrough, is positioned within the sleeve 37. The element 40 may have additional ducts for receiving connecting wires 42 connected to the sensing electrode 14 and the reference electrode 18, respectively, as well as connecting wires 43 for the heater element 25. The wires 42, 43 extend from the connection end portion of the spacer and support element 40.

At the side facing the sensor 11, they are angled over the edge surface 44 of the support body 40 to form contact portions 45. The contact portions 45 can be secured in position on suitable recesses or grooves formed in the support and spacer 40; in any event, they should be so positioned that no electrical connection can occur between the electrode connecting wires 42 and the heater connecting wires 43.

A shoulder 46 is formed at the connecting end portion of the support body 46. A disk spring 47 is placed on the shoulder 40, the disk spring extending over and beyond the circumference of the body 40. The disk spring 47 engages the bottom 38 of the sleeve 37 to provide a compressive force and mechanical bias and to hold all the elements securely in position. The counter force of the disk spring is taken up by the lips or projections 36 engaging into the recess 35 of the metallic socket 34.

Other arrangements to hold the sensors together may be used. The arrangement described is preferred due to simplicity and reliability. It is also possible, for example, to secure the heater element carrier directly on the end portion adjacent the measuring end of the housing 32 by attachment in any well known manner, for example by peening or hammering-over, and to carry out the connecting wires separately to suitable connection terminals. It is also possible to secure the heater element carrier 22 to the outer side of the solid electrolyte tube 11.

The particular type of seal between the solid electrolyte tube 11' and the housing 32 and the heater element carrier 22, respectively, by means of copper-coated steel rings 29 also is a preferred structural assembly, but other seals may be used.

Various changes and modifications may be made, particularly if the sensor is to be adapted to different types of constructions, as described, for example, in the aforementioned U.S. Pat. No. 4,157,282 and the German Patent Disclosure Documents, respectively.

We claim:

1. Heated gas composition sensor structure, particularly to determine the composition of combustion exhaust gases, especially for association with an internal combustion engine having a sensing element (11) made of temperature-dependent ceramic including a solid electrolyte body (11') of tubular form, and electrodes (14, 18) applied to different surface regions of said tubular body;

and a heating element (25) to heat the sensor element (11) including a tubular carrier (22) surrounding the sensor element, wherein the wall thickness of the tubular carrier (22) is between 0.3 and 0.8 mm;

the heating element (25) is secured to the inner wall of the tubular carrier (22);

and the distance between the inner wall of the heating element and the outer surface of the sensing element (11) is, as a maximum, 1 mm.

2. Sensor structure according to claim 1, wherein said distance between the heating element (25) and the outer surface of the sensing element (11) is less than 0.5 mm.

3. Sensor structure according to claim 1, wherein the carrier tube comprises an insulating ceramic.

4. Sensor structure according to claim 1 or 2 or 3, wherein the heater element (25) is positioned at the inner surface (21) of the carrier tube (22) in a spiral or meander-shaped path.

5. Sensor structure according to claim 4, wherein the heater element (25) comprises a wire.

6. Sensor structure according to claim 4, wherein the tubular carrier (22) is formed with a bottom (23) at the end exposed to the gas to be analyzed, said bottom being formed with an aperture (25) to permit exposure of said solid electrolyte sensor (11) to the gas to be analyzed.

7. Sensor structure according to claim 1, wherein the tubular carrier (22) is formed with a bottom (23) at the end exposed to the gas to be analyzed, said bottom being formed with an aperture (25) to permit exposure of said solid electrolyte sensor (11) to the gas to be analyzed.

8. Sensor structure according to claim 1, wherein the tubular carrier (22) for the heater element (25) is formed with a shoulder (28);

a socket (32) is provided formed with a matching shoulder (30) surrounding a central bore (31);

and a sealing element (29) is provided, located between the shoulder (30) of the socket and the shoulder (28) on the tubular carrier.

9. Sensor structure according to claim 8, wherein the solid electrolyte body (11') is formed with a flange matching the shoulder (28) on the tubular carrier (22) for the heater element;

and a sealing element (19) is provided, positioned between the flange (13) of the solid electrolyte body (11') and the surface (20) of the shoulder of the heater element carrier tube (22).

10. Sensor structure according to claim 9, wherein the tubular carrier (22) comprises an insulating ceramic.

11. Sensor structure according to claim 1, wherein the distance between the heating element (25) and the outer surface of the sensing element (11) is less than 0.5 mm;

the wall thickness of the tubular carrier (22) is about 0.6 mm;

and the tubular carrier (22) comprises an insulating ceramic.

* * * * *